US011746094B2

(12) United States Patent (10) Patent No.: US 11,746,094 B2
Vendrell et al. (45) Date of Patent: Sep. 5, 2023

(54) SMALL MOLECULE PHOTOSENSITIZERS FOR PHOTODYNAMIC THERAPY

(71) Applicant: The University Court of the University of Edinburgh, Edinburgh (GB)

(72) Inventors: Marc Vendrell, Edinburgh (GB); Antonio Fernandez, Edinburgh (GB); Sam Benson, Edinburgh (GB); Nicole D. Barth, Edinburgh (GB); Fabio De Moliner, Edinburgh (GB)

(73) Assignee: The University Court of the University of Edinburgh, Edinburgh (GB)

(*) Notice: Subject to any disclaimer, the term of this patent is extended or adjusted under 35 U.S.C. 154(b) by 75 days.

(21) Appl. No.: 17/439,069

(22) PCT Filed: Mar. 17, 2020

(86) PCT No.: PCT/EP2020/057300
§ 371 (c)(1),
(2) Date: Sep. 14, 2021

(87) PCT Pub. No.: WO2020/187913
PCT Pub. Date: Sep. 24, 2020

(65) Prior Publication Data
US 2022/0153714 A1 May 19, 2022

(30) Foreign Application Priority Data
Mar. 18, 2019 (GB) ..................... 1903671

(51) Int. Cl.
*A61K 41/00* (2020.01)
*C07D 293/12* (2006.01)
*C07D 421/04* (2006.01)
(52) U.S. Cl.
CPC ........ *C07D 293/12* (2013.01); *A61K 41/0057* (2013.01); *C07D 421/04* (2013.01)
(58) Field of Classification Search
None
See application file for complete search history.

(56) References Cited

U.S. PATENT DOCUMENTS 3,532,610 A 10/1970 Du Rose

FOREIGN PATENT DOCUMENTS

| CN | 103242260 A | 8/2013 |
|---|---|---|
| CN | 107759642 A | 3/2018 |
| CN | 108164570 A | 6/2018 |
| CN | 109350742 A | 2/2019 |
| JP | 2011-184374 A | 9/2011 |
| WO | WO-2009/034396 A2 | 3/2009 |
| WO | WO-2018/122232 A1 | 7/2018 |

OTHER PUBLICATIONS

PubChem CID 129889859, National Center for Biotechnology Information. PubChem Compound Summary for CID 129889859, Phenylpiazselenol. https://pubchem.ncbi.nlm.nih.gov/compound/Phenylpiazselenol. Accessed Jan. 30, 2023, create date Sep. 13, 2017. (Year: 2017).*
Bella, M., et al., "Application of the Gould-Jacobs reaction to 4-amino-2,1,3-benzoselenadiazole," Tetrahedron, 66(41):8169-8174 (2010) (6 pages).
Bella, M., et al., "Synthesis of 9-ethyl[1,2,5]selenadiazolo[3,4,h]quinolones by the application of modified Gould-Jacobs reaction to the N-ethyl1-2,1,3-benzoselenadiazol-4-amine," ARKIVOC, 2014(5):181-198 (2014) (18 pages).
Benson, S., et al., "SCOTfluors: Small, Conjugatable, Orthogonal, and Tunable Fluorophores for In Vivo Imaging of Cell Metabolism," Angewandte Chemie, Int. Ed., 58(21):6911-6915 (2019) (5 pages).
Davies, K., et al., "Umpolung of o-phenylenediamines by conversion into isobenzimidazole. An expedient approach to heterocycles with nucleophilic substituents," J. Chem. Soc., 2465-2474 (1984) (11 pages).
Idris, I., et al., "Effective modulation of the photoluminescence properties of 2,1,3-benzothiadiazoles and 2,1,3-benzoselenadiazoles by Pd-catalyzed C—H bond arylations," J. Mat. Chem., 6(7):1731-1737 (2018) (7 pages).
International Search Report and Written Opinion on PCT/EP2020/057300 dated May 14, 2020 (16 pages).
Lesko, J., et al., "Mass Spectra of Some 4- and 5-Substituted Derivatives of Benzoselenadiazoles," Molecules, 5(12):937-940 (2000) (4 pages).

(Continued)

*Primary Examiner* — Samantha L Shterengarts
(74) *Attorney, Agent, or Firm* — Foley & Lardner LLP (57) ABSTRACT

The invention relates to small photosensitizers, their process of preparation and uses of the compounds in optical imaging and photodynamic therapy. The invention provides a compound of formula (I), a derivative or a salt thereof Wherein $R_1$ is selected from the group consisting of amines, anilines, phenols, thiophenols, selenols and aryl groups; $R_2$ and $R_3$ independently are H or halogen; $R_4$ is selected from the group consisting of H, nitro and cyano: and $R_5$ and $R_6$ independently are either absent or oxygen or methyl.

16 Claims, 7 Drawing Sheets

(56) References Cited

OTHER PUBLICATIONS

Ramadoss, V., et al., "Total synthesis of kealiiquinone: the regio-controlled strategy for accessing its 1-methyl-4-arylbenzimidazolone core," RSC Advances, 8(54):30761-30776 (2018) (16 pages).

Sawicki, E., et al., "Structure of 2,1,3-Benzoselenadiazole and Its Derivatives. II. Position of the Proton 1," J. Org. Chem., 22(5):507-509 (1957) (3 pages).

Shuck-Lee, D., et al., "Heterocyclic Compounds That Inhibit Rev-RRE Function and Human Immunodeficiency Virus Type 1 Replication," Antimicrobial Agents and Chemotherapy, 52(9):3169-3179 (2008) (11 pages).

Yan, X., et al., "Palladium(II)-catalyzed arylation of unactivated C(sp3)-H bonds by using 2,1,3-benzoselenadiazole-4-amine as directing ligand," Tetrahedron Letters, 58(1):54-58 (2016) (5 pages).

\* cited by examiner

U87-mCrimson

U87-mCrimson + light

U87-mCrimson + PS-SCOTfluor13 + light

Figure 7

SMALL MOLECULE PHOTOSENSITIZERS FOR PHOTODYNAMIC THERAPY

CROSS-REFERENCE TO RELATED PATENT APPLICATIONS

This application is a U.S. National Phase Application under 35 U.S.C. § 371 of International Application No. PCT/EP2020/057300, filed Mar. 17, 2020, which claims the benefit of and priority to GB Appl. No. 1903671.4, filed on Mar. 18, 2019, each of which are incorporated herein by reference in their entirety.

FIELD OF THE INVENTION

The invention relates to small and neutral potent photosensitizers. The invention further relates to processes for the preparation of the compounds and uses of the compounds in optical imaging and photodynamic therapy. Still further the invention relates to a method for making a photosensitive compound starting from a common scaffold selenobenzodiazole modified with electron-donating groups.

BACKGROUND OF THE INVENTION

Photodynamic therapy (PDT) is a treatment that uses a photosensitizer and a particular type of light. When photosensitizers are exposed to a specific wavelength of light, they produce a form of oxygen that kills nearby cells.

A wide number of photosensitisers (PS) have been developed. However, a very few are seeing regular use within contemporary clinical practice due to their intrinsic limitations, including lack of selectivity, systemic phototoxicity, and large molecular size that impedes conjugation to small biomolecules like metabolites, peptides or nucleic acids.

For instance, one important strategy in the development of cancer-targeting therapies is to harness the Warburg effect, which is related to a considerable rise in glucose uptake and is observed in the majority of tumours. This metabolic effect is particularly prevalent within glioblastomas, where malignant brain cells take up large amounts of glucose.

Whereas the preparation of PS based on chlorins and porphyrins has been widely described, its conjugation to glucose is hampered by the large size and charges of the photosensitive scaffolds, which leads to a reduction in both the recognition of glucose transporters and limited tissue permeability (e.g., crossing blood brain barrier), which is essential for effective therapies.

Therefore, there is still the need for photosensitizers, which allow conjugation to small biomolecules like metabolites, peptides or nucleic acids, are selective and do not have systemic phototoxicity,

STATEMENT OF THE INVENTION

The present invention provides compounds, which are small enough to retain the transport and uptake properties of small biomolecules including metabolites.

The compound of the invention can be used in photodynamic therapy for ablation of metabolically-active cells. Once the labelled metabolites are uptaken by the target cells, their activation with visible light leads to singlet oxygen generation and concomitant cell death.

The compounds of the invention can also be used to label cancer cells, immune cells as well as stem cells for cell-based therapies or fluorescence-guided surgery. They are also suitable to be used for other optical imaging modalities beyond fluorescence. For example, they can be used as multimodal reagents as they can be readily detected under Surface-Enhanced Raman Scattering upon conjugation to metal surfaces.

In particular, it is hereby provided a compound of formula (I), a derivative or a salt thereof (I)

wherein $R_1$ is selected from the group consisting of amines, anilines, phenols, thiophenols, selenols and aryl groups;

$R_2$ and $R_3$ independently are H or a halogen;

$R_4$ is selected from the group consisting of H, nitro and cyano; and $R_5$ and $R_6$ independently are either absent, or oxygen or methyl.

Preferably $R_1$ is an amine or an aniline.

Preferably $R_2$ and/or $R_3$ are/is H.

Preferably $R_4$ is nitro.

Preferably $R_5$ and/or $R_6$ are/is absent.

The compound is preferably selected from the group consisting of PS-SCOTfluor-1 to PS-SCOTfluor-20 reported below, and a derivative or a salt thereof.

PS-SCOTfluor-1

PS-SCOTfluor-2

PS-SCOTfluor-14

PS-SCOTfluor-15

PS-SCOTfluor-16

PS-SCOTfluor-17

PS-SCOTfluor-18

PS-SCOTfluor-19

PS-SCOTfluor-20

More preferably the compound is selected from the group consisting of a derivative and a salt of the PS-SCOTfluor-1 to 20 as defined above.

Even more preferably, the compound is selected from the group consisting of PS-SCOTfluor-12, 13, 16, 17 and 19 as defined above, and a derivative or a salt thereof.

Generally, the compounds of the invention may be prepared by a process comprising the step of:
a) providing an intermediate of formula II (II)

wherein, R2, R3 and R4 are as defined above. R is a halogen atom, and preferably is Br, Cl or F; R2 and R3 are preferably both H and R4 is preferably nitro;
b) linking the two amino groups by reaction with $SeO_2$ or other selenium derivatives;
c) performing a substitution reaction to replace the halogen with a nucleophile group. The preferred nucleophile groups are amines or anilines.

The present invention also provides a dye-labelled agent or a dye-labelled molecule comprising a compound of the invention, a derivative or a salt thereof.

Further the invention provides a general method for making a photosensitiser to be used in photodynamic therapy or optical imaging, which comprises the conjugation of a scaffold of formula II with a biomolecule selected from the group consisting of metabolites, saccharides, lipids, proteins, antibodies, peptides, nucleic acids, aptamers and nanoparticles, depending on the cells to be targeted.

The method comprises linking the two amino groups in the scaffold by reaction with $SeO_2$ or other selenium derivatives, preferably the linking happens before the conjugation of the scaffold with the biomolecule.

Preferably the biomolecules are conjugated via an amino group. Some biomolecules already have inherent amino groups (e.g. proteins, peptides), some others can be conjugated using an amino-containing spacer.

Preferably the compound is a derivative of an amino acid, peptide, protein, glucose, lactic acid or biolipid.

In another embodiment the invention provides the above described compound, a derivative or a salt thereof for use in optical imaging and photodynamic therapy.

In another embodiment the invention provides the above described compound, a derivative or a salt thereof for use in a therapeutic, diagnostic, surgery or analytical method.

The methods are preferably optical imaging or photodynamic therapy.

Preferably the method is fluorescent probes for diagnosis of protein aggregates in neurodegenerative diseases.

The method could also be selected from the group consisting of fluorescence spectroscopy, fluorimetry, fluorescence microscopy, fluorescence tomography, whole-body fluorescence imaging, flow cytometry, fluorescence-assisted cell sorting, fluorescence-guided surgery, fluorescence endomicroscopy.

Preferably, the method comprises labelling, tracking, imaging biomolecules as well as generating singlet oxygen in cells and tissues in vivo, in vitro or ex vivo. More preferably in vivo.

Conveniently, the method is photodynamic therapy for the treatment of diseases, preferably cancer.

A further embodiment of the invention relates to a diagnostic method comprising administering (e.g. local or systemic administration) to an organism, preferably a mammal dye-labelled agent associated to disease biomarkers comprising a compound of formula (I), and identifying them with an appropriate technique (e.g. fluorescence spectroscopy, fluorimetry, fluorescence microscopy, fluorescence tomography, whole-body fluorescence imaging, flow cytometry, fluorescence-assisted cell sorting, fluorescence-guided surgery, fluorescence endomicroscopy and photodynamic therapy) in a relevant biological sample (e.g. blood, biopsy, tissue, lavage) in order to diagnose a diseased state or stratify patients according to different disease states.

The present invention also provides surgery methods comprising the steps of administration to a mammal a dye-labelled agent (e.g. local or systemic administration), identification by an appropriate method (e.g. fluorescence spectroscopy, fluorimetry, fluorescence microscopy, fluorescence tomography, whole-body fluorescence imaging, flow cytometry, fluorescence-assisted cell sorting, fluorescence-guided surgery, fluorescence endomicroscopy and photodynamic therapy) and subsequent choice of an appropriate surgical treatment, including fluorescence-guided surgery and photodynamic therapy.

The present invention further provides therapeutic methods comprising administration to a mammal of a compound of the invention, a derivative or a salt thereof linked to a molecule with biological activity (e.g. metabolites, saccharides, lipids, proteins, antibodies, peptides, nucleic acids, aptamers or nanoparticles) to identify optimal administration routes and dosage by means of fluorescence spectroscopy, fluorimetry, fluorescence microscopy, fluorescence tomography, whole-body fluorescence imaging, flow cytometry, fluorescence-assisted cell sorting, fluorescence-guided surgery, fluorescence endomicroscopy and photodynamic therapy.

The present invention also provides analytical method to characterize dye-labelled molecules by fluorescence spectroscopy, fluorimetry, fluorescence microscopy, fluorescence tomography, whole-body fluorescence imaging, flow cytometry, fluorescence-assisted cell sorting, fluorescence-guided surgery, fluorescence endomicroscopy and photodynamic therapy.

Anyone of the methods described herewith may comprise labelling, tracking, imaging biomolecules as well as generating singlet oxygen in cells and tissues in vivo, in vitro or ex vivo.

The present invention further provides a method for imaging of cells in vivo said method comprises the steps of administration of dye-labelled agents (e.g. local or systemic administration) and identification by an appropriate method (e.g. fluorescence spectroscopy, fluorimetry, fluorescence microscopy, fluorescence tomography, whole-body fluorescence imaging, flow cytometry, fluorescence-assisted cell sorting, fluorescence-guided surgery, fluorescence endomicroscopy and photodynamic therapy).

The present invention further provides a pharmaceutical formulation comprising the compound of formula (I), a derivative or a salt thereof and a pharmaceutically acceptable carrier.

A pharmaceutically acceptable carrier may be for example physiological sterile saline solution, sterile water solution, pyrogen-free water solution, isotonic saline solution, and phosphate buffer solution.

The present invention further provides the pharmaceutical formulation comprising the compound of formula (I), a derivative or a salt thereof and a pharmaceutically acceptable carrier for use in the therapeutic, diagnostic, surgery or analytical method described above.

The present invention further provides a kit said kit comprising the compound of the invention, a derivative or a salt thereof as described above as a photosensitizer reagent for biomolecules and/or cells, aqueous buffers and/or solvent for reconstitution, packaging materials and instructions for use thereof.

DEFINITIONS

As used herein, the term "derivative" is used to refer to the residue of a chemical compound, such as an amino acid, after it has undergone chemical modification. For instance, these could include derivatives incorporating linkers with reactive groups for bioconjugation (e.g. amines, carboxylic acids, succinimidyl esters, maleimides, azides, alkynes, tetrazines), as well as derivatives of antibodies, proteins, peptides and small molecules.

As used herein, the term "salt" is used to refer to an assembly of cations and anions. These could include sodium, ammonium, quaternary ammonium, calcium, magnesium and potassium as cations or iodine, chloride, bromide, formate, perchlorate, hydrochlorate, sulfate, hydroxide, phosphate and trifluoroacetate as anions. The salt may only include the compound or the derivative of the invention and an anion. The salt may also include additional cations and anions. Preferred cations are of sodium and ammonium. Preferred anions are of iodine, bromide, formate and trifluoroacetate.

The compounds of the invention and listed above include stereoisomeric mixtures as well as single enantiomers or diastereoisomers. Preferably the compounds are (S)-enantiomers for amino acids, (D)-glucose and (L)-lactic acid.

EXAMPLES

The preparation of PS-SCOTfluors was achieved in two synthetic steps from a common intermediate of formula II. The detailed preparation of the PS-SCOTfluors is described below as well as the analytical methods used in the examples.

Materials and Synthesis

Commercially available reagents were used without further purification. Thin-layer chromatography was conducted on Merck silica gel 60F254 sheets and visualized by UV (254 and 365 nm). Silica gel (particle size 35-70 µm) was used for column chromatography. $^1$H and $^{13}$C spectra were recorded in a Bruker Avance 500 spectrometer (at 500 and 126 MHz, respectively). Data for $^1$H NMR spectra are reported as chemical shift δ (ppm), multiplicity, coupling constant (Hz), and integration. Data for $^{13}$C NMR spectra are reported as chemical shifts relative to the solvent peak. HPLC-MS analysis was performed on a Waters Alliance 2695 separation module connected to a Waters PDA2996 photo-diode array detector and a ZQ Micromass mass spectrometer (ESI-MS) with a Phenomenex column ($C_{18}$, 5 µm, 4.6×150 mm). Semipreparative scale HPLC purifications were carried out using a Waters semipreparative HPLC system fitted with a Phenomenex column ($C_{18}$ Axial, 10 µm, 21.2×150 mm) and employing UV detection.

Synthesis and Characterization of PS-SCOTfluor-1,2,3

4-(4-methoxyphenoxy)-7-nitrobenzo[c][1,2,5]selenadiazole (PS-SCOTfluor-1)

4-Fluoro-7-nitrobenzo[c][1,2,5]selenadiazole (20 mg, 0.08 mmol) was dissolved in MeCN (2 mL). 4-Methoxyphenol (12 mg, 0.08 mmol) was then added, followed by triethylamine (14 µL, 0.08 mmol) and reaction was stirred at r.t. for 1.5 h. Volatiles were removed under reduced pressure and the crude product was purified by column chromatography (HEX:EtOAc 8:2→7:3).

$^1$H NMR (500 MHz, DMSO-$d_6$) δ 8.56 (d, J=8.5 Hz, 1H), 7.29 (d, J=9.1 Hz, 2H), 7.10 (d, J=9.1 Hz, 2H), 6.59 (d, J=8.5 Hz, 1H), 3.82 (s, 3H).

$^{13}$C NMR (126 MHz, DMSO-$d_6$) δ 157.6, 156.8, 153.4, 152.3, 147.3, 135.5, 131.4, 122.5, 116.0, 106.8, 56.0.

m/z (ESI): calcd for $C_{13}H_{10}N_3O_4Se^+$ $[M+H]^+$: 352.0, found: 352.0.

4-((4-methoxyphenyl)thio)-7-nitrobenzo[c][1,2,5]selenadiazole (PS-SCOTfluor-2)

4-Fluoro-7-nitrobenzo[c][1,2,5]selenadiazole (20 mg, 0.08 mmol) was dissolved in MeCN (2 mL). 4-Methoxythiophenol (10 µL, 0.08 mmol) was then added, followed by triethylamine (14 µL, 0.08 mmol). A red precipitate was immediately formed, and after 5 min stirring at r.t. it was collected by filtration and washed with MeCN.

$^1$H NMR (500 MHz, DMSO-$d_6$) δ 8.39 (d, J=8.1 Hz, 1H), 7.65 (d, J=8.1 Hz, 2H), 7.20 (d, J=8.1 Hz, 2H), 6.64 (d, J=8.1 Hz, 1H), 3.87 (s, 3H).

$^{13}$C NMR (126 MHz, DMSO-$d_6$) δ 161.6, 156.8, 150.4, 146.7, 137.9, 137.6, 128.8, 119.5, 118.1, 116.7, 56.0.

m/z (ESI): calcd for $C_{13}H_{10}N_3O_3SSe^+$ $[M+H]^+$: 368.0, found: 367.9.

4-(4-methoxyphenyl)-7-nitrobenzo[c][1,2,5]selenadiazole (PS-SCOTfluor-3)

4-Chloro-7-nitrobenzo[c][1,2,5]selenadiazole (20 mg, 0.08 mmol) and 4-methoxyphenylboronic acid (12 mg, 0.08 mmoll) were placed in a round bottom flask fitted with a reflux condenser under a $N_2$ atmosphere. Dioxane (2 mL) was then added via a syringe and the mixture was stirred, followed by addition of $CsCO_3$ (74 mg, 0.24 mmoll) and $Pd(PPh_3)_4$ (20% wt.). Reaction was then heated at 100° C. for 2 h. It was then cooled down to room temperature, diluted with brine (25 mL) and extracted with EtOAc (3×25 mL). The organic layer was dried over anhydrous $MgSO_4$, the solvent was removed under reduced pressure and the crude product was purified by column chromatography (DCM:Hex 1:1→DCM).

$^1$H NMR (500 MHz, DMSO-d$_6$) δ 8.57 (d, J=7.8 Hz, 1H), 7.97 (d, J=8.9 Hz, 2H), 7.80 (d, J=7.8 Hz, 1H), 7.14 (d, J=8.9 Hz, 2H), 3.87 (s, 3H).

$^{13}$C NMR (126 MHz, DMSO-d$_6$) δ 160.8, 159.2, 151.6, 141.5, 139.6, 135.0, 131.9, 129.4, 128.8, 128.3, 124.9, 114.5, 55.8.

m/z (ESI): calcd for $C_{13}H_{10}N_3O_3Se^+$ [M+H]$^+$: 335.0, found: 335.0.

General Method for the Preparation of PS-SCOTfluor-4-20

4-Fluoro-7-nitrobenzo[c][1,2,5]selenadiazole (0.08 mmol) was dissolved in MeCN (1 mL). The corresponding amine (0.12 mmol) was then added as well N,N-diethylamine (22 μL, 0.12 mmol) and reaction was stirred at r.t. for 5 mins. Upon completion, volatiles were removed under reduced pressure and the products were purified by column chromatography (DCM:MeOH 98:2)

N,N-diethyl-7-nitrobenzo[c][1,2,5]selenadiazol-4-amine (PS-SCOTfluor-5)

$^1$H NMR (500 MHz, DMSO-d$_6$) δ 8.50 (d, J=9.4 Hz, 1H), 6.48 (d, J=9.4 Hz, 1H), 4.01 (q, J=7.0 Hz, 4H), 1.32 (t, J=7.0 Hz, 6H).

$^{13}$C NMR (126 MHz, DMSO-d$_6$) δ 153.9, 152.4, 148.7, 134.1, 128.2, 101.9, 47.8, 13.2. m/z (ESI): calcd for $C_{10}H_{12}N_4O_2SeNa^+$ [M+Na]$^+$: 323.0, found: 323.1.

N,N-diethyl-6-iodo-7-nitrobenzo[c][1,2,5]selenadiazol-4-amine (PS-SCOTfluor-6)

$^1$H NMR (500 MHz, DMSO-d$_6$) δ 6.65 (s, 1H), 3.89 (q, J=7.0 Hz, 4H), 1.26 (t, J=7.0 Hz, 6H).

$^{13}$C NMR (126 MHz, DMSO-d$_6$) δ 153.2, 151.8, 144.0, 137.1, 112.1, 98.9, 47.00, 13.1.

m/z (ESI): calcd for $C_{10}H_{12}IN_4O_2Se^+$ [M+H]$^+$: 426.9, found: 426.8.

N-cyclohexyl-7-nitrobenzo[c][1,2,5]selenadiazol-4-amine (PS-SCOTfluor-7)

$^1$H NMR (500 MHz, DMSO-d$_6$) δ 8.50 (d, J=9.1 Hz, 1H), 6.67 (d, J=9.2 Hz, 1H), 4.06-4.01 (m, 4H), 1.73 (s, 6H).

$^{13}$C NMR (126 MHz, DMSO-d$_6$) δ 153.6, 153.3, 150.4, 133.4, 130.1, 104.8, 51.3, 26.3, 24.4.

m/z (ESI): calcd for $C_{11}H_{13}N_4O_2Se^+$ [M+H]$^+$: 312.2, found: 312.4.

(R)-2-hydroxy-3-((7-nitrobenzo[c][1,2,5]selenadiazol-4-yl)amino)propanoic acid (PS-SCOTfluor-12)

$^1$H NMR (500 MHz, DMSO-d$_6$) δ 8.60 (d, J=8.9, 1H), 7.99 (t, J=6.0, 1H), 6.48 (d, J=9.0, 1H), 4.38 (dd, J=7.2, 4.5, 1H), 3.82-3.59 (m, 2H). $^{13}$C NMR (126 MHz, DMSO-d$_6$) δ 174.2, 152.3, 148.7, 135.5, 129.0, 98.4, 69.1, 46.8, 40.9.

m/z (HRMS ESI): calcd. for $C_9H_9N_4O_5Se^+$ [M+H]$^+$: 332.9727, found: 332.9769.

(2R,3R,4R,5S,6R)-6-(hydroxymethyl)-3-((7-nitrobenzo[c][1,2,5]thiadiazol-4-yl)amino)tetrahydro-2H-pyran-2,4,5-triol (PS-SCOTfluor-13)

$^1$H NMR (500 MHz, DMSO-d$_6$) δ 8.55 (d, J=7.4 Hz, 1H), 7.03 (s, 1H), 6.57 (d, J=7.4 Hz, 1H), 5.17 (s, 2H), 5.10-5.03 (m, 1H), 4.52-4.45 (m, 1H), 3.85-3.65 (m, 4H), 3.50-3.47 (m, 1H).

$^{13}$C NMR (126 MHz, DMSO-d$_6$) 152.1, 148.5, 135.6, 128.7, 99.0, 90.5, 73.3, 73.0, 70.8, 61.5, 58.2.

m/z (HRMS ESI): calcd for $C_{12}H_{15}N_4O_7S^+$ [M+H]$^+$: 359.0656, found: 359.0687.

(2R,3R,4R,5S,6R)-3-(ethyl(7-nitrobenzo[c][1,2,5]selenadiazol-4-yl)amino)-6-(hydroxymethyl)tetrahydro-2H-pyran-2,4,5-triol (PS-SCOTfluor-14)

$^1$H NMR (500 MHz, Methanol-d$_4$) δ 8.63 (d, J=9.2 Hz, 1H), 8.62 (d, J=9.2 Hz, 1H), 6.77 (d, J=9.2 Hz, 1H), 6.66 (d, J=9.4 Hz, 1H), 5.73 (d, J=3.2 Hz, 1H), 5.59-5.52 (m, 1H), 5.42 (dd, J=10.7, 3.3 Hz, 1H), 5.07 (d, J=8.1 Hz, 1H), 4.19 (dd, J=10.7, 8.4 Hz, 1H), 4.10 (dd, J=14.6, 7.2 Hz, 1H), 4.01-3.85 (m, 6H), 3.79-3.72 (m, 2H), 3.49-3.42 (m, 2H), 3.38-3.35 (m, 2H), 1.37 (t, J=7.0 Hz, 3H), 1.33 (t, J=6.9 Hz, 3H).

$^{13}$C NMR (126 MHz, Methanol-d$_4$) δ 154.0, 153.9, 153.8, 153.6, 150.9, 150.6, 133.2, 133.0, 129.9, 129.7, 105.4, 104.7, 94.5, 93.5, 76.5, 72.9, 72.3, 71.7, 70.6, 67.2, 65.4, 61.4, 40.5, 11.8, 11.1.

m/z (ESI): calcd for $C_{14}H_{19}N_4O_7Se^+$ [M+H]$^+$: 435.0, found 435.1.

2-amino-3-((7-nitrobenzo[c][1,2,5]selenadiazol-4-yl)amino)propanoic acid (PS-SCOTfluor-19)

$^1$H NMR (500 MHz, DMSO-d$_6$) δ 8.66 (br, s, 1H), 8.61 (d, J=8.9 Hz, 1H), 8.25 (br, t, J=5.9 Hz, 1H), 6.60 (d, J=8.9 Hz, 1H), 4.26 (t, J=5.7 Hz, 1H), 4.13-3.87 (m, 2H).

$^{13}$C NMR (126 MHz, DMSO-d$_6$) δ 169.6, 152.5, 152.1, 148.2, 135.1, 129.7, 98.5, 51.6, 43.1. m/z (HRMS ESI): calcd for $C_9H_{10}N_5O_4Se^+$ [M+H]$^+$: 331.9892, found 331.9895.

Photosensitizer Characterization

Phototoxicity assays of nitrobenzodiazoles (NBD) with different bridging groups (X) listed below was evaluated in U87 glioblastoma cells. All compounds were administered at 100 μM and illuminated for 10 min under 520 nm light.

X = O, S, Se and C(CH$_3$)$_2$

U87 cells were plated at 20,000 cells per well in a 96 well plate in Dulbecco's modified Eagle's medium (DMEM) supplemented with 10% FBS, 100 U mL$^{-1}$ penicillin and 0.1 mg mL$^{-1}$ streptomycin. Once the cells had reached 90% confluency, the media was replaced by Krebs-Ringer bicarbonate buffer (KRB) (129 mM NaCl, 4.7 mM KCl, 1.2 mM KH$_2$PO$_4$, 5 mM NaHCO$_3$, 10 mM HEPES; 2.5 mM CaCl$_2$, 1.2 mM MgCl$_2$ and 0.2% BSA, pH 7.4). Appropriate compounds were added to the wells at the indicated concentrations. After 1 h, wells were illuminated using a ThorLabs M530L3 LED torch for 10 mins at 10 mW. After illumination, media was removed and replaced with supplemented DMEM. Cell viability was measured 24 h later by a conventional MTT assay.

Figure 1:
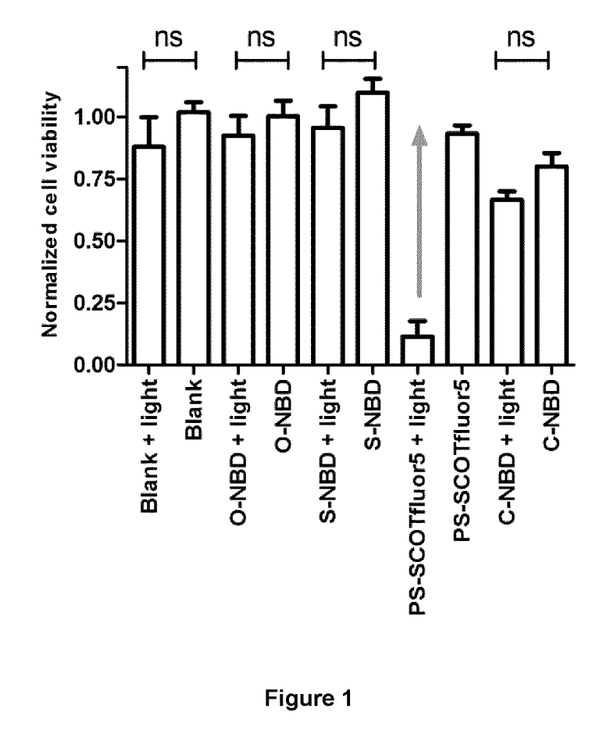
FIG. 1 shows phototoxicity assays of PS-SCOTfluor-5 and NBD analogues with different bridging groups in U87 glioblastoma cells. Compounds were administered at 100 µM and cells were illuminated or not under 520 nm light for 10 min. Cell viability was determined by means of an MTT assay.

As shown in FIG. 1, Se-bridging atom is essential for effective PDT.

Figure 2:
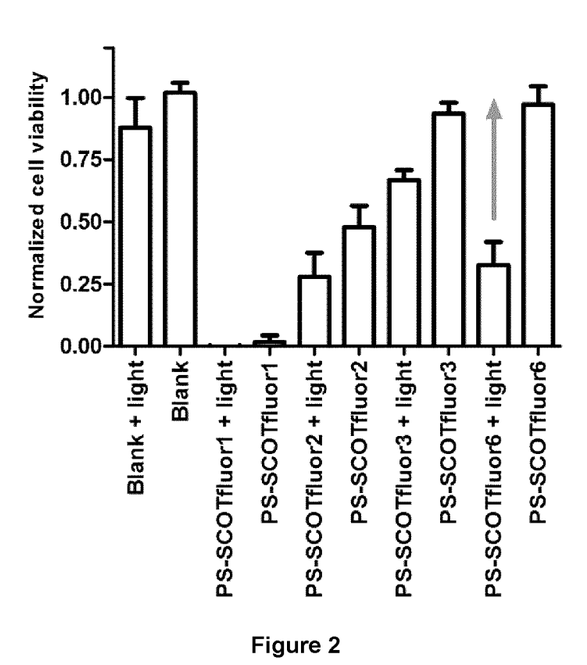
FIG. 2 shows phototoxicity assays of PS-SCOTfluor-1,2,3 and 6 in U87 glioblastoma cells. Compounds were administered at 100 µM and cells were illuminated or not under 520 nm light for 10 min. Cell viability was determined by means of an MTT assay.

Phototoxicity assays evaluation of the compounds listed below in U87 glioblastoma cells has demonstrated that amines are the most effective PDT among SeNBD dyes (FIG. 2).

Y = piperidine, anisole, thioanisole, p-methoxyaryl

Spectral Characterization of SeNBD-Amines Conjugated to Bioactive Molecules

Singlet oxygen generation was determined as a measurement of PS efficacy. Individual wells in a 96 well plate containing DPBF (40 μM) and compounds in EtOH were illuminated using a 520 nm laser with an incident power of 0.3 mW for 4, 2, 1 and 0.5 mins. The absorption of DPBF at 410 nm was measured using a Biotek Synergy H1 Hybrid Reader before (Abs$_0$) and after (Abs$_t$) illumination. The absorption of compounds (Abs$_{PS}$) was measured at 520 nm.

These values were introduced to equation 1 to give the rate of singlet oxygen production (k$_{PS}$).

$$\ln\left(\frac{Abs_t}{Abs_0}\right) \times \ln Abs_{PS} = k_{PS} I \quad (1)$$

k$_{PS}$ was then introduced to equation 2 alongside the k value of a reference photosensitiser (k$_{ref}$) and its φ$_Δ$ (φ$_{Δref}$) to give the singlet oxygen quantum yield of the PS (φ$_{ΔPS}$).

$$\Phi_{\Delta PS} = \Phi_{\Delta ref} \frac{k_{PS}}{k_{ref}} \quad (2)$$

The compounds listed below were analysed and compared to 2-NBDG, which is a commercial glucose derivative with no photosensitive properties (shown below).

2-NBDG

TABLE 1

| Compound | Singlet oxygen quantum yield (%) |
|---|---|
| PS-SCOTfluor-5 | 3% |
| PS-SCOTfluor-6 | 5% |
| PS-SCOTfluor-13 | 24% |
| PS-SCOTfluor-19 | 10% |
| 2-NBDG | <1% |

Table 1 shows that PS-SCOTfluor-13 is a glucose derivative with high activity as photosensitizer.

Cell-Based Assays

Figure 3:
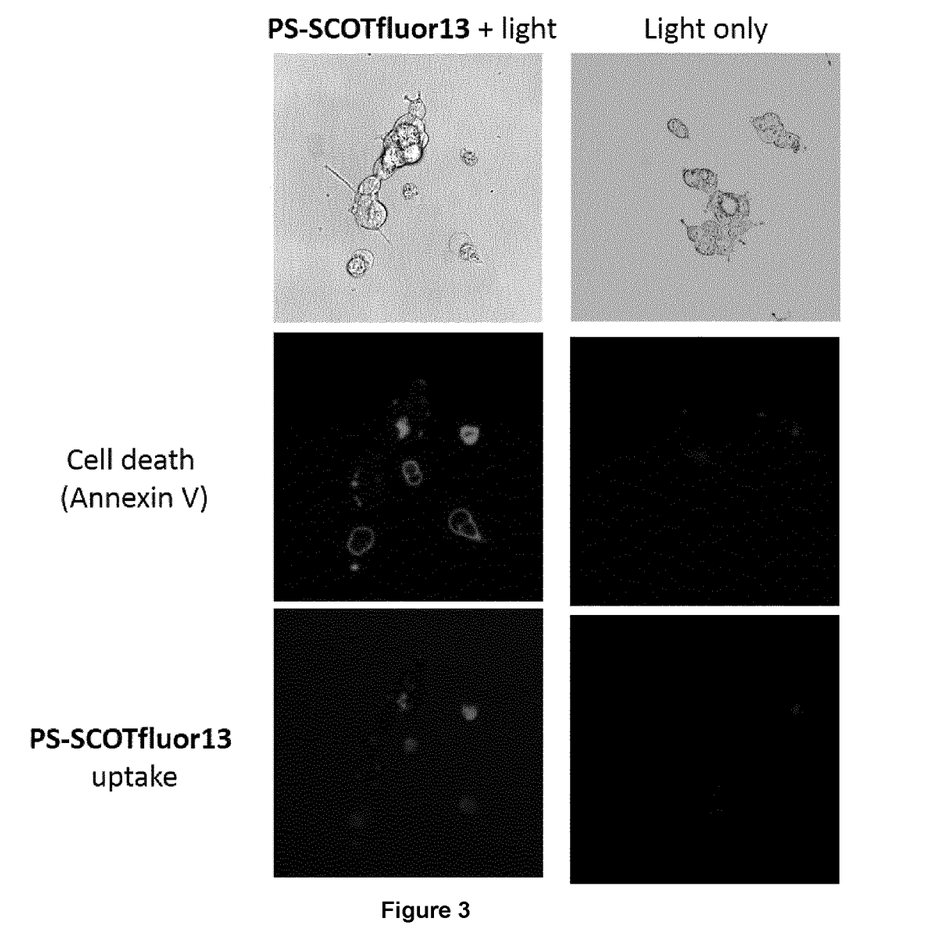
FIG. 3 shows fluorescence microscopy phototoxicity assays of PS-SCOTfluor-13 in U87 glioblastoma cells. Compound was administered at 100 µM and illuminated under 520 nm light. Annexin V-Pacific Blue was used as a stain for dead cells. Red fluorescence was used to confirm uptake of PS-SCOTfluor-13 into cells. PS-SCOTfluor-13 showed to kills U87 glioblastoma cells only after irradiation with light. Light alone does not induce any cell death as detected by Annexin V staining.
Figure 4:
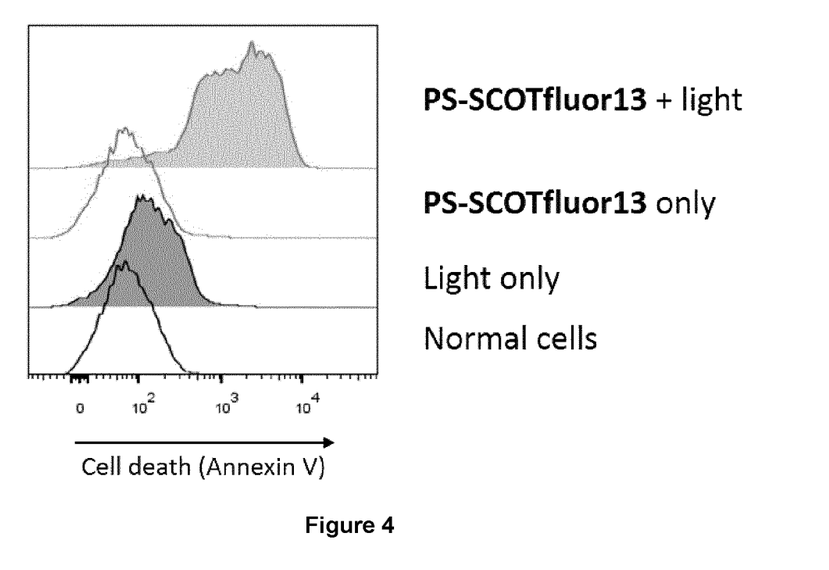
FIG. 4 shows flow cytometry phototoxicity assays of PS-SCOTfluor-13 in U87 glioblastoma cells. Compound was administered at 100 µM and illuminated under 520 nm light. Annexin V-Pacific Blue was used as a stain for dead cells. Red fluorescence was used to confirm uptake of PS-SCOTfluor-13 into cells. PS-SCOTfluor-13 showed to kills U87 glioblastoma cells only after irradiation with light but not without light. Light alone does not induce any cell death as detected by Annexin V staining.

Phototoxicity assays of PS-SCOTfluor-13 and 2-NBDG in U87 glioblastoma cells were determined. Compounds administered at 100 μM and illuminated under 520 nm light. Annexin V-Pacific Blue was used as a stain for dead cells. Red fluorescence (for PS-SCOTfluor-13) and green fluorescence (for 2-NBDG) was used to confirm uptake of the compounds into cells. PS-SCOTfluor-13 showed to kills U87 glioblastoma cells only after irradiation with light. Light alone does not induce any cell death as detected by Annexin V staining (FIG. 3 for fluorescence microscopy and FIG. 4 for flow cytometry data).

Figure 5:
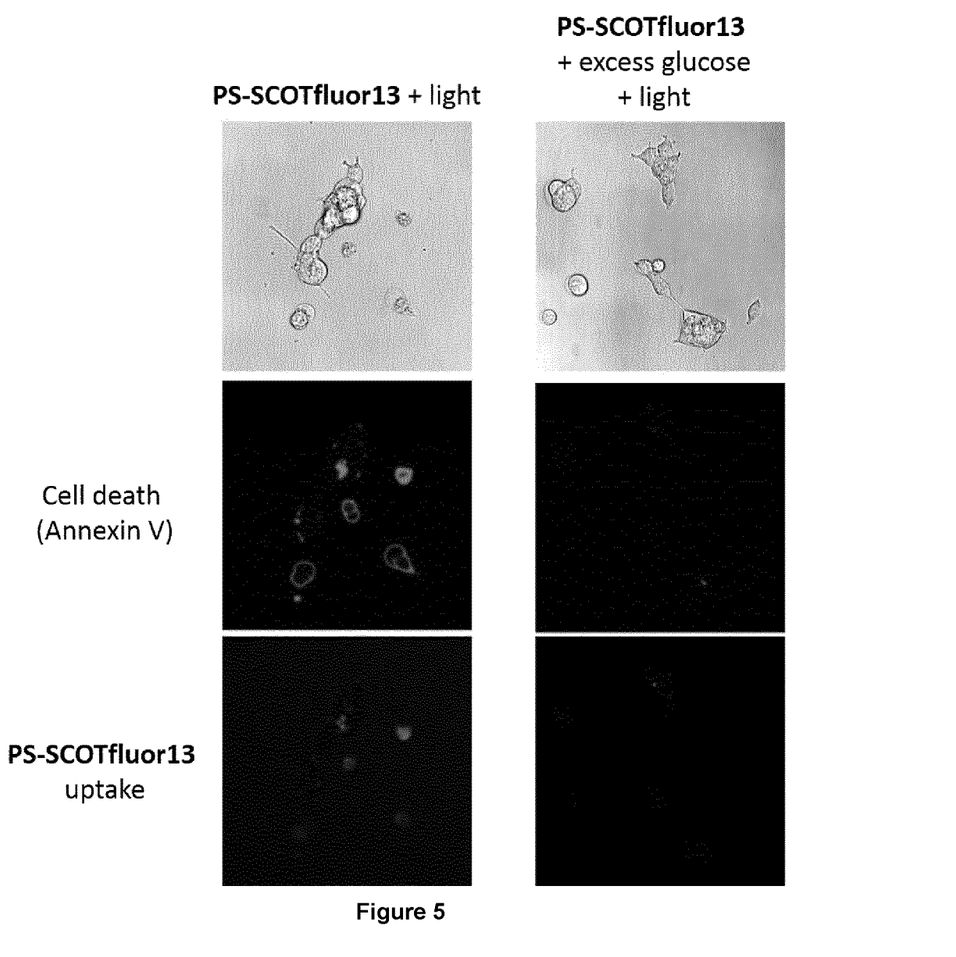
FIG. 5 shows fluorescence microscopy phototoxicity assays of PS-SCOTfluor-13 in U87 glioblastoma cells. Excess unlabelled glucose directly competes with PS-SCOTfluor-13 for transporter recognition in U87 glioblastoma cells and reduces the uptake of PS-SCOTfluor-13 and subsequently cell death as indicated by Annexin V staining.
Figure 6:
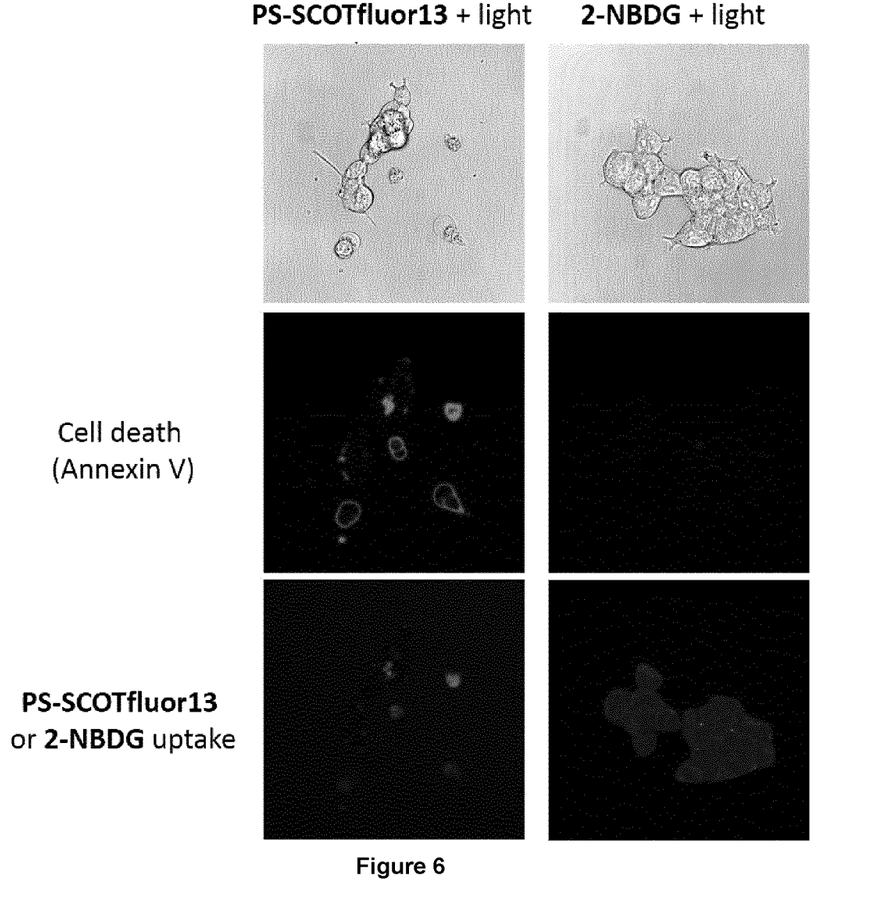
FIG. 6 shows fluorescence microscopy images of the phototoxic effect of PS-SCOTfluor-13 in U87 glioblastoma cells but not with 2-NBDG (glucose derivative without Se atom) under the same illumination protocol. 2-NBDG is also uptaken by U87 glioblastoma cells but does not kill the cells after illumination as indicated by Annexin V staining.

Excess unlabelled glucose directly competes with PS-SCOTfluor-13 for transporter recognition in U87 glioblastoma cells and reduces the uptake of PS-SCOTfluor-13 and subsequently cell death (FIG. 5). 2-NBDG (glucose derivative without Se atom) is also uptaken by U87 glioblastoma cells but does not kill the cells after illumination (FIG. 6).

Figure 7:
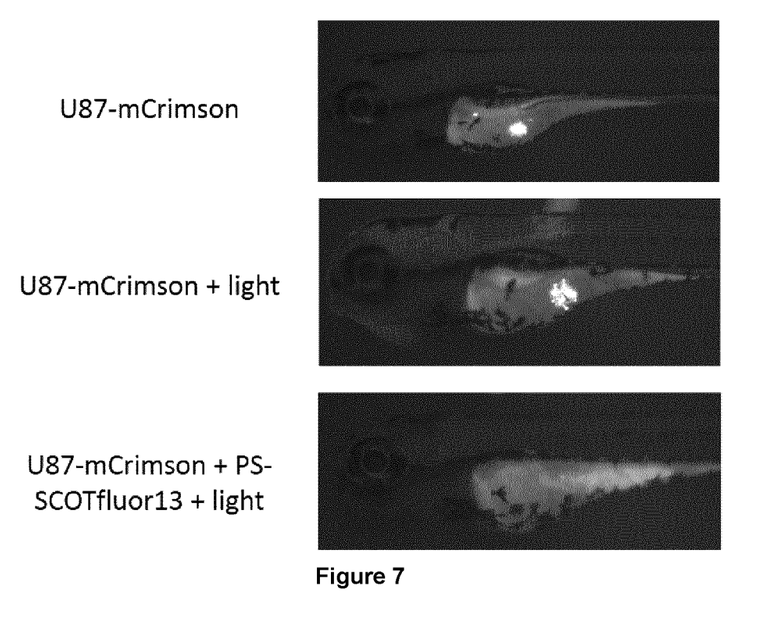
FIG. 7 shows that PS-SCOTfluor-13 kills U87-mCrimson glioblastoma cells in vivo in zebrafish. Briefly, U87-mCrimson glioblastoma cells were injected into the yolk sac of zebrafish embryos. Cells were effectively transplanted as shown by fluorescence microscopy images. Zebrafish were then irradiated with 520 nm light alone or injected with PS-SCOTfluor-13 and then irradiated with 520 nm light. Only those zebrafish that were treated with PS-SCOTfluor-13 and light show a reduction of the glioblastoma transplant as indicated by the loss of fluorescence from the mCrimson reporter.

PS-SCOTfluor-13 showed to kills U87 glioblastoma cells in vivo in zebrafish. Briefly, U87-mCrimson glioblastoma cells were injected into the yolk sac of zebrafish embryos. Cells were effectively transplanted as shown by fluorescence microscopy images. Zebrafish were then irradiated with 520 nm light alone or injected with PS-SCOTfluor-13 and then irradiated with 520 nm light. Only those zebrafish that were treated with PS-SCOTfluor-13 and light show a reduction of the glioblastoma transplant as indicated by the loss of fluorescence from the mCrimson reporter (FIG. 7).

The invention claimed is:

1. A method of treating a disease in a metabolically active cell, using targeted photodynamic therapy, wherein the method comprises:

a) providing to the metabolically-active cell a compound of formula (I)

(I)

or a derivative or a salt thereof; and b) activating the compound with visible light, resulting in singlet oxygen generation and concomitant cell death;

wherein

R1 is selected from the group consisting of amines, anilines, phenols, thiophenols, selenols and aryl groups;

R2 and R3 independently are H or halogen;

R4 is nitro; and

R5 and R6 independently are either absent or oxygen or methyl.

2. The method according to claim 1 wherein R1 is an amine or an aniline.

3. The method according to claim 1 wherein R4 is nitro.

4. The method according to claim 1 wherein R2 and/or R3 are/is H.

5. The method according to claim 1 wherein R5 and/or R6 are/is absent.

6. The method compound according to claim 1 which is selected from the group consisting of the following compounds:

PS-SCOTfluor-1

PS-SCOTfluor-2

PS-SCOTfluor-3

PS-SCOTfluor-4

PS-SCOTfluor-5

PS-SCOTfluor-6

PS-SCOTfluor-7

PS-SCOTfluor-8 and a derivative or a salt thereof.

7. The method according to claim 6 which is selected from the group consisting of the following compounds:

PS-SCOTfluor-12

PS-SCOTfluor-13

PS-SCOTfluor-16

PS-SCOTfluor-17

PS-SCOTfluor-19 and a derivative or a salt thereof.

8. The method according to claim 1 wherein the method further comprises one or more of labelling biomolecules, tracking biomolecules, and imaging biomolecules.

9. The method of claim 1 wherein the disease is cancer.

10. The method of claim 1 wherein the compound is conjugated to a biomolecule via R1.

11. The method of claim 10 wherein the biomolecule is selected from a group consisting of metabolites, saccharides, lipids, proteins, antibodies, peptides, nucleic acids, aptamers, derivative thereof and nanoparticles.

12. The method of claim 10 wherein the biomolecule is a derivative of an amino acid, peptide, protein, glucose, lactic acid or biolipid.

13. The method of claim 1 wherein the compound is small enough to retain the transport and uptake properties of the biomolecule.

14. The method of claim 1 wherein the compound of formula (I) is neutral.

15. The method of claim 1 wherein R1 is an amine and the conjugation of the metabolite to the compound is;

a) via an amino group, b) via an inherent amino group present in the metabolite, or;

c) via an amino-containing spacer.

16. The method of claim 8 wherein the metabolically active cell is in vivo, in vitro, or ex vivo.

* * * * *

UNITED STATES PATENT AND TRADEMARK OFFICE
CERTIFICATE OF CORRECTION

| | | |
|---|---|---|
| PATENT NO. | : 11,746,094 B2 | Page 1 of 1 |
| APPLICATION NO. | : 17/439069 | |
| DATED | : September 5, 2023 | |
| INVENTOR(S) | : Marc Vendrell et al. | |

It is certified that error appears in the above-identified patent and that said Letters Patent is hereby corrected as shown below:

In the Claims

In Claim 6, at Column 15, Line 37, please delete the term "compound"

Signed and Sealed this
Thirty-first Day of October, 2023

Katherine Kelly Vidal
*Director of the United States Patent and Trademark Office*